(12) United States Patent
Jarvis et al.

(10) Patent No.: US 10,294,160 B2
(45) Date of Patent: May 21, 2019

(54) MANUFACTURING OF A CERAMIC ARTICLE FROM A METAL PREFORM OR METAL MATRIX COMPOSITE PREFORM PROVIDED BY 3D-PRINTING OR 3D-WEAVING

(71) Applicant: European Space Agency, Paris (FR)

(72) Inventors: David John Jarvis, Voorschoten (NL); Wayne Eric Voice, Nottingham (GB); Nicholas John Elsworth Adkins, Nantwich (GB); Hany Salamam Sayed Ali Hassanin, Birmingham (GB)

(73) Assignee: European Space Agency, Paris (FR)

( * ) Notice: Subject to any disclaimer, the term of this patent is extended or adjusted under 35 U.S.C. 154(b) by 298 days.

(21) Appl. No.: 15/101,678

(22) PCT Filed: Dec. 4, 2013

(86) PCT No.: PCT/EP2013/075550
§ 371 (c)(1),
(2) Date: Jun. 3, 2016

(87) PCT Pub. No.: WO2015/081996
PCT Pub. Date: Jun. 11, 2015

(65) Prior Publication Data
US 2017/0022111 A1   Jan. 26, 2017

(51) Int. Cl.
*C04B 35/01* (2006.01)
*B22F 3/105* (2006.01)
(Continued)

(52) U.S. Cl.
CPC ............... *C04B 35/01* (2013.01); *A61F 2/28* (2013.01); *A61L 27/10* (2013.01); *A61L 27/56* (2013.01);
(Continued)

(58) Field of Classification Search
CPC .............. C04B 35/01; C04B 35/58085; C04B 35/5154; C04B 35/5805; C04B 35/553;
(Continued)

(56) References Cited

U.S. PATENT DOCUMENTS

| 4,713,360 A | 12/1987 | Newkirk |
| 4,808,558 A | 2/1989 | Park |

(Continued)

FOREIGN PATENT DOCUMENTS

| EP | 1252952 A2 | 10/2002 |
| WO | WO 2009/023226 A2 | 2/2009 |
| WO | WO 2009/108913 A2 | 9/2009 |

OTHER PUBLICATIONS

Ghouse, et al., The influence of laser parameters and scanning strategies on the mechanical properties of a stochastic porous material, Materials and Design, 2017, pp. 498-508.
(Continued)

*Primary Examiner* — Moshe Wilensky
(74) *Attorney, Agent, or Firm* — Woodard, Emhardt, Henry, Reeves & Wagner, LLP

(57) ABSTRACT

The present invention relates to a method of manufacturing a ceramic article (3) from a metal or metal matrix composite preform (1) provided by 3D-printing or by 3D-weaving. The preform (1) is placed in a heating chamber (2), and a predetermined time-temperature profile is applied in order to controllably react the preform (1) with a gas introduced into the heating chamber (2). The metal, the gas and the time-temperature profile are chosen so as to induce a metal-gas reaction resulting in at least a part of the preform (1) transforming into a ceramic. Preferred embodiments of the invention comprises a first oxidation stage involving a metal-gas reaction in order to form a supporting oxide layer (5) at the surface of the metal, followed by a second stage in which the heating chamber (2) is heated to a temperature (Continued)

above the melting point of the metal to increase the kinetics of the chemical reaction. The invention also relates to a number of advantageous uses of a ceramic article manufactured as described.

17 Claims, 5 Drawing Sheets

(51) Int. Cl.
| | |
|---|---|
| C04B 35/547 | (2006.01) |
| C04B 35/553 | (2006.01) |
| C04B 35/56 | (2006.01) |
| C04B 35/58 | (2006.01) |
| C04B 35/65 | (2006.01) |
| C04B 38/00 | (2006.01) |
| B22F 3/11 | (2006.01) |
| B22F 5/00 | (2006.01) |
| A61F 2/28 | (2006.01) |
| A61L 27/10 | (2006.01) |
| A61L 27/56 | (2006.01) |
| C04B 35/515 | (2006.01) |
| B22F 1/02 | (2006.01) |
| C04B 111/00 | (2006.01) |
| B33Y 10/00 | (2015.01) |
| B33Y 80/00 | (2015.01) |
| C23C 8/10 | (2006.01) |

(52) U.S. Cl.
CPC .............. *B22F 3/1055* (2013.01); *B22F 3/11* (2013.01); *B22F 5/007* (2013.01); *C04B 35/5154* (2013.01); *C04B 35/547* (2013.01); *C04B 35/553* (2013.01); *C04B 35/56* (2013.01); *C04B 35/58* (2013.01); *C04B 35/5805* (2013.01); *C04B 35/58085* (2013.01); *C04B 35/65* (2013.01); *C04B 38/0025* (2013.01); *A61F 2310/00011* (2013.01); *B22F 1/025* (2013.01); *B33Y 10/00* (2014.12); *B33Y 80/00* (2014.12); *C04B 2111/00982* (2013.01); *C04B 2235/40* (2013.01); *C04B 2235/401* (2013.01); *C04B 2235/402* (2013.01); *C04B 2235/404* (2013.01); *C04B 2235/405* (2013.01); *C04B 2235/407* (2013.01); *C04B 2235/428* (2013.01); *C04B 2235/46* (2013.01); *C04B 2235/465* (2013.01); *C04B 2235/614* (2013.01); *C04B 2235/661* (2013.01); *C23C 8/10* (2013.01); *Y02P 10/292* (2015.11); *Y02P 10/295* (2015.11)

(58) Field of Classification Search
CPC ......... C04B 35/56; C04B 35/58; C04B 35/65; C04B 35/547; C04B 35/0025; A61L 27/56; A61L 27/10; A61F 2/28; B22F 5/007; B22F 3/11; B22F 3/1055; B33Y 10/00; B33Y 80/00
See application file for complete search history.

(56) References Cited

U.S. PATENT DOCUMENTS

| | | |
|---|---|---|
| 4,882,306 A | 11/1989 | Kennedy |
| 5,447,291 A | 9/1995 | Sandhage |
| 2015/0013144 A1* | 1/2015 | Bush ................ C22F 1/183 29/527.1 |
| 2015/0030493 A1* | 1/2015 | Scott ................ A61L 27/56 419/2 |

OTHER PUBLICATIONS

Yang, et al, Simple method to generate and fabricate stochastic porous scaffolds, Materials Science and Engineering C, 2015, pp. 444-450.

\* cited by examiner

MANUFACTURING OF A CERAMIC ARTICLE FROM A METAL PREFORM OR METAL MATRIX COMPOSITE PREFORM PROVIDED BY 3D-PRINTING OR 3D-WEAVING

FIELD OF THE INVENTION

The present invention relates to a method of manufacturing a ceramic article from a metal preform or metal matrix composite preform provided by 3D-printing or 3D-weaving. The preform is exposed to a heat treatment in a gas atmosphere which induces a metal-gas reaction resulting in at least a part of the preform transforming into a ceramic.

BACKGROUND OF THE INVENTION

Some of the work leading to the present invention was done within the field of thruster technology for space applications. Here the decompositions of the propellant, such as hydrazine or hydrogen peroxide, is activated by passing the propellant over a hot catalytic bed containing PGM elements, such as platinum, palladium, or iridium. The current state-of-the-art is to use a powdered ceramic material containing an active catalyst and to press the loose powder between metallic top and bottom gauzes in order to make a porous powder pack. One of the known problems with loose powder in between gauzes is that the powder can sometimes remove itself and fall out of the thruster into the exhaust system. This leads to an accelerated degradation of the pack, a reduction in its performance, as well as fine powdered material being emitted as space debris.

An alternative is open-cell ceramic foams which can be used in applications such as catalytic converters for exhaust treatment and other high-temperature applications taking advantage of the high-temperature and chemical resistance as well as the high strength-to-weight ratios achievable by the ceramic foams. It is known from U.S. Pat. No. 4,808,558 to manufacture ceramic foam from an open-cell, reticulated precursor metal. Hereby ceramic articles of randomly interconnected cells or channels have been made. The inner structure of such an article is closely related to the available types of metal foams. Furthermore such random structure may result in a turbulent fluid flow which can be advantageous for some applications. However, for other applications other types of flow would be desired.

Hence, an improved method of manufacturing a ceramic article would be advantageous, and in particular a method with which a high degree of freedom to design parts with controlled internal and external details previously considered too intricate. This fits with the requirement of many applications.

OBJECT OF THE INVENTION

An object of the present invention is to provide a method of manufacturing a ceramic article by which the degradation due to powder falling off from an article made from ceramic powder can be avoided.

Another object of the present invention is to provide a method of manufacturing a ceramic article by which a higher control of the inner structure of a porous or lattice-type ceramic article is available than what is possible with prior art methods.

It is an object of at least some embodiments of the present invention is to provide a method of manufacturing a ceramic article by which a higher porosity of a controllably structured material is achievable than what is possible with prior art methods.

It is another object of at least some embodiments of the present invention to provide a method of manufacturing a ceramic article by which incorporation of additives e.g. in the form of metallic or ceramic particles into the preform makes it possible to enhance the solid-gas-reaction. This can e.g. enable building of ceramic articles of larger thicknesses than what is possible with prior art methods.

It is a further object of the present invention to provide an alternative to the prior art.

In particular, it may be seen as an object of the present invention to provide a method of manufacturing a ceramic article that solves the above mentioned problems of the prior art.

SUMMARY OF THE INVENTION

Thus, the above described object and several other objects are intended to be obtained in a first aspect of the invention by providing a method of manufacturing a ceramic article, the method comprising the steps of:
   providing a metal or metal matrix composite preform,
   placing the preform in a heating chamber,
   heating the heating chamber by applying a predetermined time-temperature profile in order to controllably react the preform with a gas introduced into the heating chamber,
wherein the metal, the gas and the time-temperature profile are chosen so as to induce a metal-gas reaction resulting in at least a part of the preform transforming into a ceramic, and
wherein the preform is provided by 3D-printing or by 3D-weaving.

For some embodiments of the invention, all of the transformation of metal into ceramic takes place inside the heating chamber, whereas for other embodiments, a first stage of the transformation takes place before the preform is placed in the heating chamber to have the predetermined time-temperature applied. This will be explained in further details below.

By "preform" is preferably meant an article which has been formed into a preliminary shape defining the final, desired one.

The time-temperature profile typically comprises regions of constant temperature(s) in combination with sloping regions of increasing or decreasing temperatures. For some material combinations, it may also be appropriate to use only sloping regions with varying slopes.

An advantage of providing the preform by 3D-printing is that it is possible to maintain full control over the spatial configuration of the material. It is e.g. possible to print a lattice structure having a constant spatial configuration throughout the preform. For some applications it will be more advantageous to have a varying, such as a graded structure. This may e.g. be the case when the ceramic article is to be used for scaffolds for use in tissue engineering where a vascular structure can be advantageous e.g. to ensure an appropriate oxygen supply to all parts of an artificial tissue under manufacturing. Another example of an application where full control over the structure is advantageous is for catalytic converters. Here the controllability can be used to optimize the structure to account for any special computational fluid dynamics, CFD, characteristics of the propellant e.g. to improve the performance by minimizing the pressure drop over the catalytic converter and maximising the gas-surface contact. Such complex geometries including inner structures as are available with the present invention would not be possible with other manufacturing methods.

A main advantage of a ceramic article made by the present invention as compared to one made from powder is that the falling off of loose powder can be avoided.

In embodiments of the invention, wherein the preform is 3D-printed, it may be done by using a powder-bed, blown-powder or wire-fed additive manufacturing method. Such methods are known per se, but the use of the 3D-printed preform to be transformed into a ceramic material is not considered to be known from prior art. The 3D-printing process may deploy one or more heat sources selected from: laser, electron beam, plasma or incoherent light, to melt the metal.

The metal pre-form may be 3D-printed into a shape selected from: a lattice, an open cellular foam, a porous article, a mould or die. Examples of advantageous uses of some of these shapes are given below in relation to some of the possible uses of the invention.

When the preform is made by 3D weaving of metal wire, this is typically done by use of a loom similar to that for the manufacture of clothing fabric.

In some embodiments of the invention, the time-temperature profile comprises a first oxidation stage in which the heating chamber is heated to below the melting point of the metal to allow metal-gas reaction in order to form a supporting oxide layer at the surface of the metal, followed by a second stage in which the heating chamber is heated to a temperature above the melting point of the metal to increase the kinetics of the chemical reaction. Such increase in temperature may e.g. be necessary to ensure that the oxygen or other gas can diffuse to all parts of the preform throughout.

By use of the present invention, it is possible to obtain articles in which the grain size of the ceramic is nano-size. This is important for functional property applications as well as improving the structural strength.

In such an embodiment comprising two stages, the first stage may have a duration resulting in a thick enough oxide layer forming so that the article does not slump when heated to more elevated temperatures in the second stage, and a contiguous oxide layer forming so that the not yet reacted metal does not leak out when melting during the second stage. This two-stage process is particularly useful when the invention is used to manufacture an article having a lattice or open cell structure which would not be self-supporting at high temperatures without such a contiguous oxide layer.

In the present context, "contiguous" is preferably defined as "having a continuous boundary so that an encapsulated enclosure is obtained that is liquid impermeable", i.e. an exoskeleton of ceramic.

The two-stage method may further comprise a third stage in which the heating chamber is heated to a higher temperature than in the second stage so that phase transformation of the ceramic material takes place. Such a final stage can e.g. be used to convert alumina to the stronger gamma form of alumina.

In an alternative embodiment to the one just described, the method comprises a first stage of oxidation treatment by a chemical, electro-chemical or plasma electrolytic anodising process in order to form a supporting oxide layer at the surface of the metal before the preform is placed in the heating chamber and then placing the preform in the heating chamber, followed by a second stage in which the heating chamber is heated to a temperature above the melting point of the metal to increase the kinetics of the chemical reaction, wherein the first stage has a duration resulting in:
a thick enough oxide layer forming so that the article does not slump when heated in the second stage, and
a contiguous oxide layer forming so that the not yet reacted metal does not leak out when melting during the second stage.

Such an oxidation treatment by a chemical, electro-chemical or plasma electrolytic anodising process typically occurs within a chemical or electro-chemical cell at a relatively low temperature. Such an anodizing process also gives the opportunity of inserting chemicals into the coating such as one or more of colour dyes, catalytic chemicals and drugs.

In any of the embodiments as mentioned above, the metal-gas reaction(s) may take place at a gas pressure in the heating chamber of 0.1-10 atm, where "atm" is atmospheric pressure equalling 101,325 Pa. It may e.g. take place below atmospheric pressure, such as at a pressure of 0.1-0.9 atm; or it may take place at increased pressure, such as at 2-5 or 5-10 atm.

The preform may be fully transformed during the process to make a fully ceramic article. Alternatively the preform may be only partially transformed into ceramic to make a ceramic-metal composite. Such a composite material may e.g. be useful for applications where the electrical conductivity of the metal is needed in combination with e.g. a high chemical or wear resistance of the surrounding ceramic layer.

In embodiments wherein a partially transformed ceramic-metal composite is obtained, it may be further leached in a leaching solution, such as a caustic or acid solution, to remove any remaining metal so as to create hollow ceramic tubes. This leaching can e.g. be used as a step of increasing the porosity still further from what is feasible with 3D-printing or 3D-weaving. Articles having a high porosity can e.g. find use in microfluidic devices. The use of ceramic materials may be particularly useful for high temperature applications as well as for very low temperatures due to the very good thermal stability of ceramics.

The preform may be made of or comprise a metal, such as aluminium, zirconium, yttrium, cerium, titanium, hafnium, tungsten, vanadium, niobium, tantalum, beryllium, iron, cobalt nickel, copper, lanthanum, lead, zinc, tin, indium, silicon, germanium, magnesium, calcium or an alloy thereof. The actual choice of material will of course depend on the application. As an example, magnesium and calcium may e.g. relevant in relation to manufacturing of artificial bone structure for use in implants.

The 3D printed preform may incorporate other metal or ceramic additives in the depositing material being used to build-up the preform. Such additives may e.g. be $Al_2O_3$, SiC, $Si_3N_4$, AlN, Zr, Cr, Ti, Nb, Si, CNT or graphene. The choice of the incorporated additives, typically in the form of particles, may be based on the required properties of the final parts after being heat treated in the heating chamber or be based on their ability to enhance the solid-gas-reaction and the diffusion of this reaction inside the structures. Added elements in an alloy or particles in a composite may e.g. enhance the solid-gas-reaction by disrupting the oxide layer so that the oxygen can diffuse through faster. The required properties of the final parts which can be influenced by added elements or particles are e.g. the ion conductivity or the colour.

The gas introduced into the heating chamber may be air, oxygen, nitrogen, silane, borane, methane, ammonia, hydrogen, hydrogen sulphide, halogen, phosphine, carbon dioxide or a mixture thereof. The choice of gas depends on which ceramic article that is to be produced.

The choice of both metal and gas depends on which ceramic article that is to be produced. Some examples of possible ceramic materials are: metal-oxide, a metal-nitride, a metal-silicide, a metal-boride, a metal-carbide, a metal-hydride, a metal-sulphide, metal-phosphide, metal halide or a mixed ceramic material. Examples of particularly useful materials for selected applications are given in the detailed description.

For some embodiments of the invention, the type of gas in the heating chamber may be changed during the process so as to create a layered ceramic article of varying composition. Such a layered structure will be advantageous for an article having different requirements for the surface than for the inner structure, such as a need for a very wear resistant or chemical resistant surface and a core region having a higher fracture toughness, provided that these properties cannot be obtained in one ceramic material.

The method may further comprise a subsequent step of reacting the formed ceramic article with acid, such as liquid phosphoric acid so as to convert the metal oxide into a metal phosphate for biomedical applications.

A second aspect of the invention relates to an article manufactured according to any of the preceding claims. Such an article may e.g. be an article adapted to be used in any of the possible uses mentioned in the following.

A third aspect of the invention relates to the use of an article manufactured as described above in relation to the first aspect of the invention. Examples of such uses which at present are considered to be particularly useful will be mentioned in the following without being limiting to the scope of the other aspects of the invention and as claimed in the claims.

A possible embodiment of the third aspect is the use of an article manufactured as described above for a catalytic substrate lattice onto which an active metal catalyst is chemically washed. The active metal catalyst may e.g. be Pt, Pd, Ni, Au, Ag, Rh, Cu, Ir, Ti, or Ru. The metal catalyst would typically be coated onto the ceramic in particulate form, such as being in the form of coated nano-particles.

Another possible embodiment of the third aspect is the use of an article manufactured as described above for a casting mould. Such an article could be with build-in leachable ceramic cores. An example of such an embodiment as a mould is given in the detailed description.

Another possible embodiment of the third aspect is the use of an article manufactured as described above for a combustor, high temperature heat exchanger, heat buffer, or regenerator in a thermodynamic heat engine. For such applications it is highly advantageous to be able to combine the high-temperature properties of ceramic materials with the very high degree of freedom to design both the outer and the inner structure of a ceramic article as is possible with the present invention.

Another possible embodiment of the third aspect is the use of an article manufactured as described above for a low thermal conductivity component having a ceramic lattice optionally impregnated with an aerogel. Aerogel can impregnate the gaps in a solid fully-transformed lattice as well as the gaps in a hollow partially-transformed lattice. An example of a possible use of such an embodiment is given in relation to FIG. 10.

Another possible embodiment of the third aspect is the use of an article manufactured as described above for a medical device, such as a biomedical implant, an orthopaedic device, an artificial bone structure or a stem-cell scaffold.

For such applications it is highly advantageous to be able to precisely design the outer geometries of a device and at the same time carefully design the inner structure in order to optimise both the local strength-to-weight properties as well as the local sizes and arrangements of the voids to ensure an optimal oxygen transportation when the device is taken into use.

Another possible embodiment of the third aspect is the use of an article manufactured as described above for RF antenna, dielectric, microwave, embedded sensors and photonic applications. For some of such applications it will be advantageous to let the preform transform only partially leaving part of the electrically conductive metal material inside the ceramic.

Another possible embodiment of the third aspect is the use of an article manufactured as described above for microfluidic devices, such as tubes and interconnected networks of tubes. This will be particularly useful with the embodiments as described above where the method of manufacturing involves leaching away part of the material.

In embodiments where the article being manufactured is in the form of a ceramic lattice, it may be used as a preform, into which liquid alloy is gravity-cast or squeeze-cast via melt-infiltration in order to form a high-temperature cermet article.

Still another possible use of the invention is for water purification filters. For this application, an advantage of using a material which can withstand very high temperatures is that the filter can be cleaned by burning to remove any impurities.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The method of manufacturing a ceramic article according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
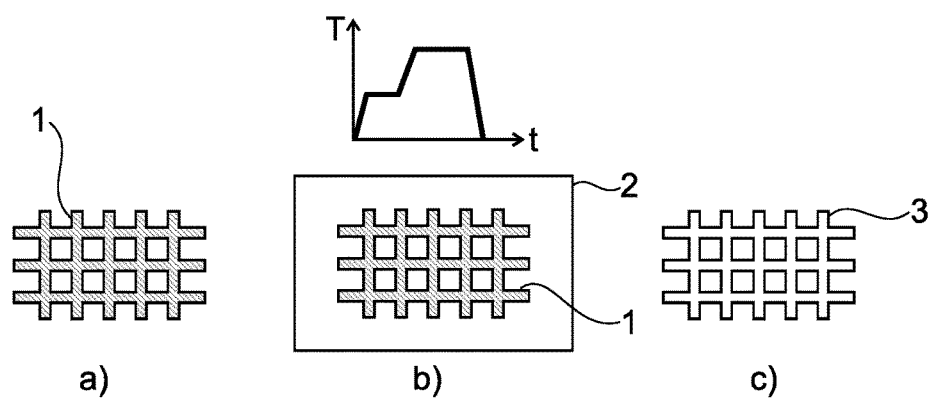
FIG. 1 shows schematically the manufacturing method in which a 3D-printed metal lattice is transformed into a ceramic article.

An overall idea behind the present invention is the possibility of transforming a 3D preform into a ceramic by applying a process involving an increased temperature which results in chemical metal-gas reactions. FIG. 1 shows schematically and in cross-sectional view the basic steps in such a method. First a preform 1 is provided as shown in FIG. 1.a. The preform 1 is shown in lattice form having a regular pattern which is available from 3D-printing, but other types of preforms will be shown below. The preform 1 is placed in a heating chamber 2, and a predetermined time-temperature profile is applied in order to controllably react the preform 1 with a gas (not shown) introduced into the heating chamber 2; this is shown in FIG. 1.b. The result is a transformation of the preform 1 into a ceramic article 3 as shown in FIG. 1.c. The metal, the gas and the time-temperature profile are chosen so as to induce a metal-gas reaction resulting in at least a part of the preform 1 transforming into a ceramic article 3.

The 3D-printing can e.g. be done by using a powder-bed, blown-powder or wire-fed additive manufacturing method, and the 3D-printing process typically deploys one or more heat sources selected from: laser, electron beam, plasma or incoherent light, to melt the metal. The actual choice may depend on what is available but also on the actual materials as some may only be available e.g. as powder.

Figure 2:
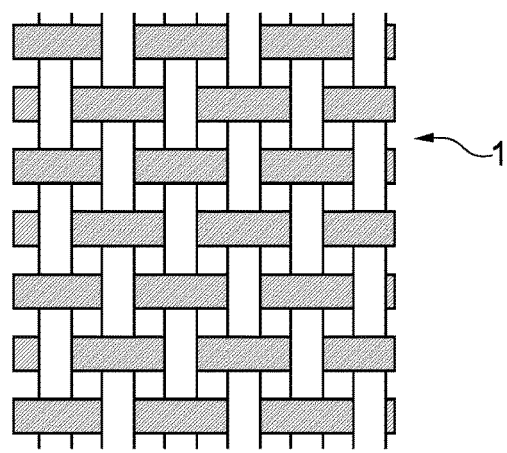
FIG. 2 shows schematically a preform made by 3D-weaving.
Figure 3:
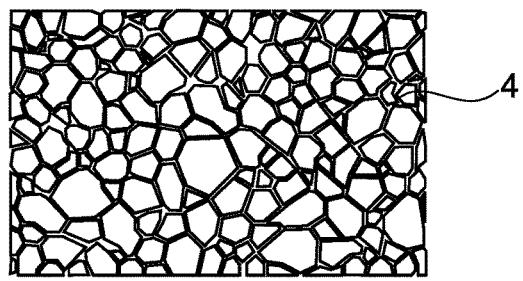
FIG. 3 shows schematically an open cellular foam as an example of a porous article which can be used as a preform.

An alternative to providing the preform 1 by 3D-printing is to use 3D-weaving of metal wire; an example of such a 3D-woven preform is shown schematically in FIG. 2. Examples of other possible types of preforms which can be obtained by 3D-printing are an open cellular foam 4 as an example of a porous article as shown in FIG. 3. Yet another example is a mould as will be shown in FIG. 10.

Figure 4:
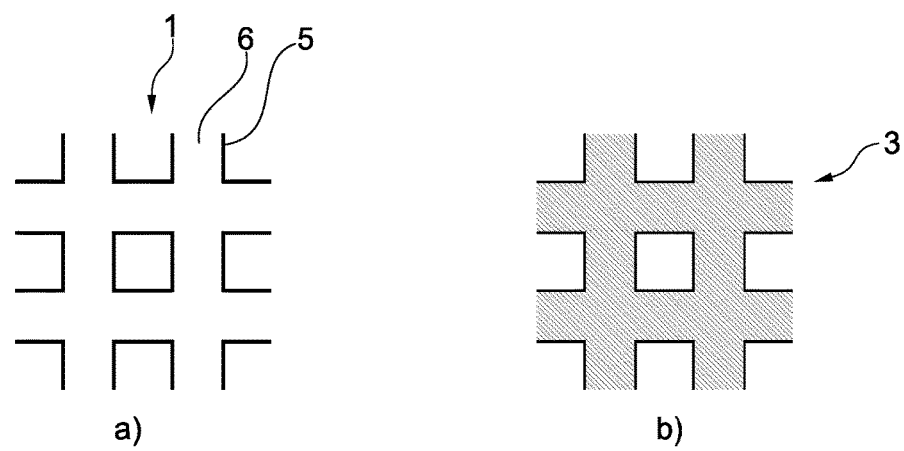
FIGS. 4.a and 4.b show schematically a lattice structure after the first and second stages, respectively, of a manufacturing method according to the present invention.

In some embodiments of the invention, the time-temperature profile comprises a first oxidation stage in which the heating chamber 2 is heated to below the melting point of the metal to allow metal-gas reaction in order to form a supporting oxide layer at the surface of the metal, followed by a second stage in which the heating chamber 2 is heated to a temperature above the melting point of the metal to increase the kinetics of the chemical reaction. This is illustrated schematically and in cross-sectional view in FIG. 4, where FIG. 4.a shows a section of the preform 1 with a supporting oxide layer 5 formed on the surface while there is still unreacted metal 6 inside the lattice and encapsulated by the oxide layer 5. The first stage has a duration resulting in a thick enough oxide forming so that the article does not slump when heated to more elevated temperatures in the second stage, and a contiguous oxide forming so that the not yet reacted metal does not leak out when melting during the second stage. In the embodiment shown in FIG. 4, the second stage has a duration so that all of the metal reacts with the gas and forms a ceramic material throughout the ceramic article 3 as shown in FIG. 4.b.

Figure 5:
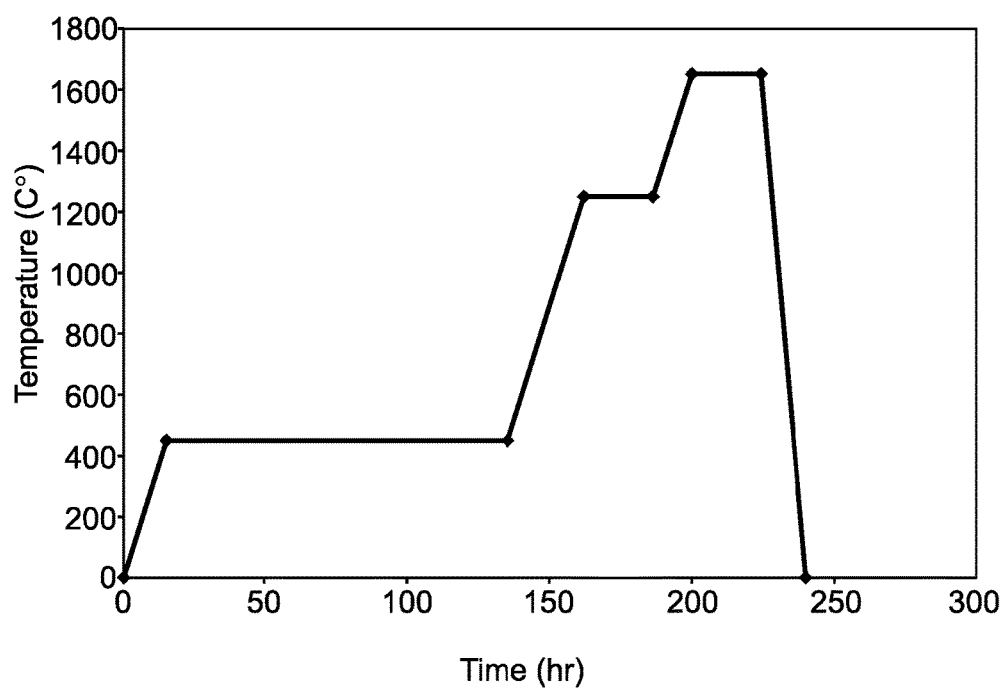
FIG. 5 shows an example of a time-temperature curve which can be used in relation to the present invention.

There may optionally be a third stage in which the heating chamber is heated to a higher temperature than in the second stage so that phase transformation of the ceramic material takes place. The three stages are shown as an exemplary time-temperature profile in FIG. 5 where the time in hours is shown along the x-axis and the temperature in ° C. in the heating chamber 2 is shown along the y-axis. In FIG. 5, there is a holding time at constant temperature in each of the stages. However, the invention also covers profiles without such a constant holding temperature in one or more of the stages. One such example would be a time-temperature profile having a slowly increasing ramp-up profile throughout or as a part of the first stage instead of the step increase followed by a horizontal course.

Figure 6:
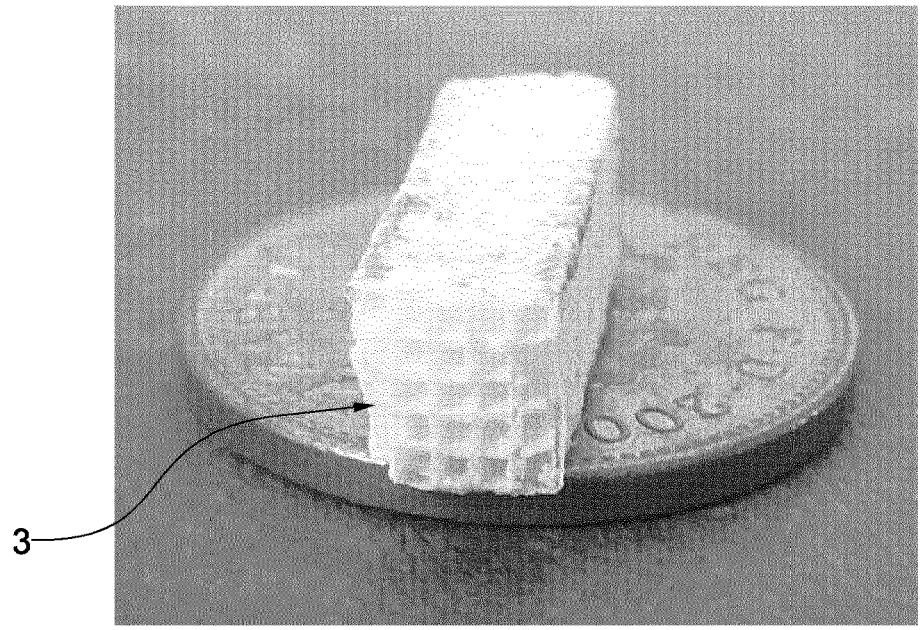
FIG. 6 shows a photo of a fully transformed ceramic article with lattice structure.

An example of a ceramic article 3 in the form of a lattice manufactured as described above is shown in FIG. 6. An aluminium precursor lattice 1 was 3D-printed using an Al-powder bed and laser melting techniques. As a next step, a low temperature heating/oxidation cycle was used to first create a thin layer 5 of $Al_2O_3$ on the outside shell of the lattice. After this, the lattice was fired to 1500° C. to melt and convert all remaining aluminium into $Al_2O_3$. The porous alumina ceramic lattice was then washed with platinum ligand chemical to wash the active Pt nanoparticles onto the substrate surface. This resulted in the final white alumina porous lattice-based catalyst as shown in FIG. 6.

Figure 7:
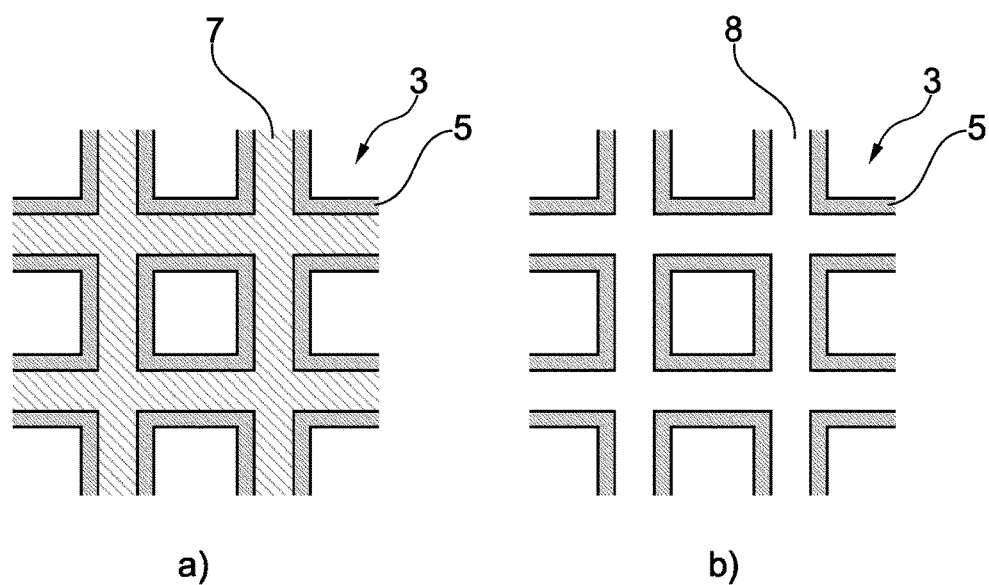
FIG. 7 shows schematically how a preform partially transformed into ceramic can be used to obtain an article having a more porous geometry than the one shown in FIG. 6.
Figure 8:
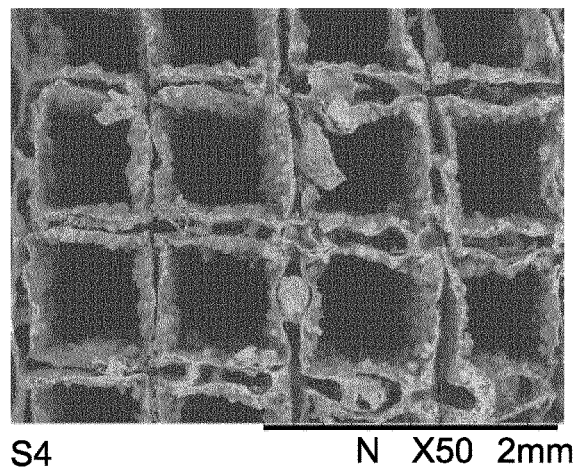
FIG. 8 shows a photo of an article made as shown in FIG. 7.

In some embodiments of the invention, the preform 1 is only partially transformed into ceramic to make a ceramic-metal composite. In this case, a cross sectional view of a lattice could look as shown schematically in FIG. 7.a where the hatched areas 7 inside the oxide layer 5 would represent non-reacted metal. Such a composite material can be used as it is for applications where the combination of properties of different types of materials is advantageous; this could e.g. be the case for turbo machinery. In other embodiments the partially transformed ceramic-metal composite is further leached e.g. in caustic solution, NaOH, to remove any remaining metal so as to create hollow ceramic tubes. This would result in a material having a more open structure corresponding to the white areas 8 inside the oxide layer 5 in FIG. 7.b being cavities. Acids and other alkali solutions may also be used for the leaching. Such a method involving leaching has been used to manufacture the specimen shown in FIG. 8. It is a SEM picture of an alumina as explained for FIG. 6 but where the second stage was stopped before all the aluminium had transformed into alumina. The specimen was leached in caustic solution while it still had some of the aluminium inside it.

For applications where high strength and stiffness is important, the most advantageous would often be to have a material that is fully transformed into ceramic or having the metal "core" areas remaining. Materials having material removed would result in a lower density and more cavities. They could e.g. find use for thermal insulation possibly in combination with aerogel being filled into the cavities.

Figure 9:
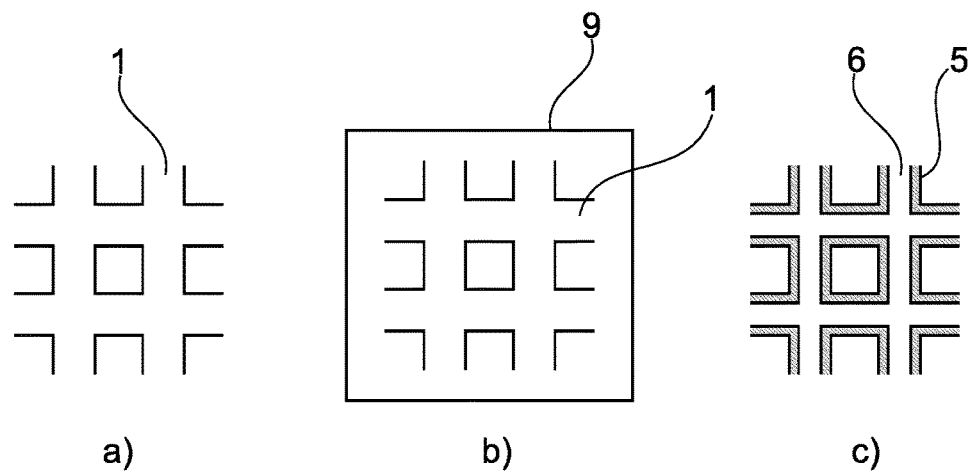
FIG. 9 shows schematically and in cross-sectional view a method comprising a first stage which is performed before the preform is placed in the heating chamber.
Figure 9:
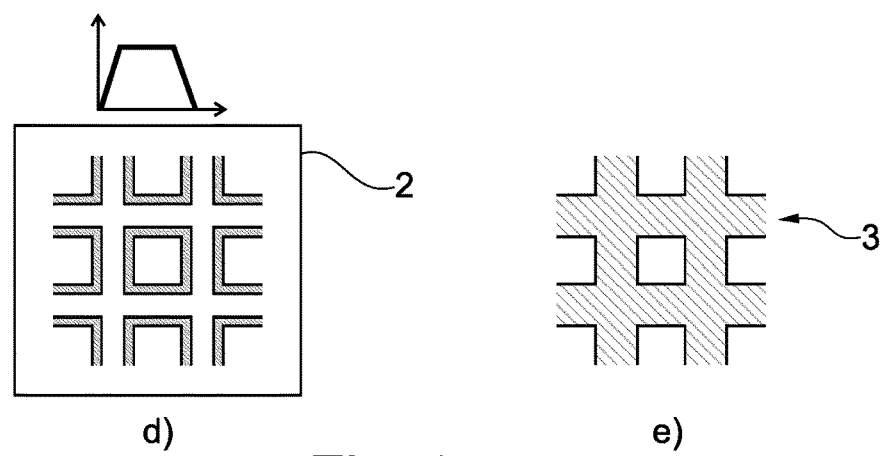

FIG. 9 shows schematically and in cross-sectional view a method in which the preform 1 as shown in FIG. 9.a is placed in a chemical or electro-chemical cell 9 to perform an oxidation treatment by a chemical, electro-chemical or plasma electrolytic anodising process; see FIG. 9.b. This results in the formation of a supporting oxide layer 5 at the surface of the metal 6 as shown in FIG. 9.c. The preform 1 with the oxide layer 5 formed thereon is then placed in the heating chamber 2—see FIG. 9.d—and the heating chamber 2 is heated to a temperature above the melting point of the metal to increase the kinetics of the chemical reaction. The resulting ceramic article 3 is shown in FIG. 9.e in an embodiment with full transformation of the metal into ceramic.

Figure 10:
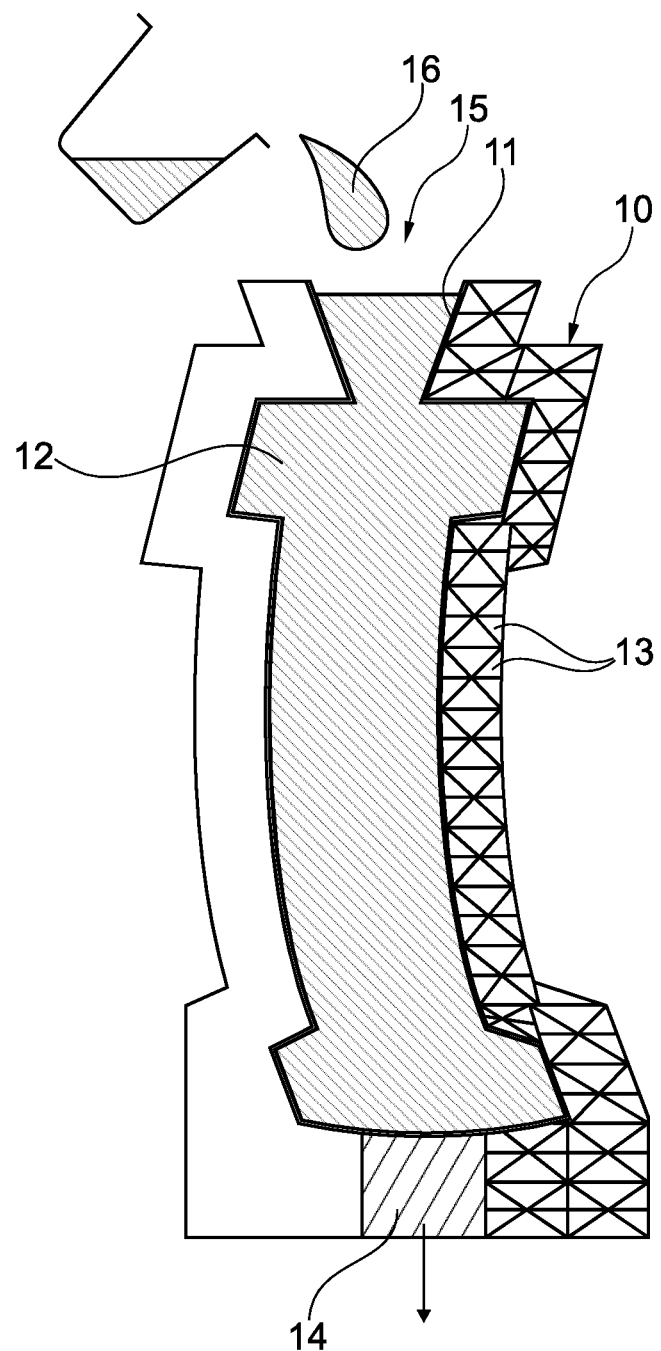
FIG. 10 shows schematically the use of a ceramic lattice shell mould manufactured according the present invention.

FIG. 10 shows a possible use of a ceramic article manufactured by a method involving 3D-printing as described above. The figure shows schematically a cross sectional view of a ceramic lattice shell mould 10. The mould 10 is designed to have a solid internal surface layer 11 which can e.g. be used to ensure a desired surface roughness of the specimen 12 being cast. This internal surface layer 11 can be integrated already in the 3D-printed preform 1. The cavities 13 in the ceramic article forming the sides of the mould 10 may be filled with aerogel to further improve the thermal insulation properties. The mould 10 shown in the figure has a region of solid metal 14 at the lower end which acts as a heat extraction chill during casting. The removal of heat from the specimen during casting may be further improved by using a water cooled lower part. The use of such a mould 10 having insulating sides combined with a heat extraction chill 14 at the bottom side of the mould 10, i.e. opposite the open upper end 15 through which liquid alloy 16 is poured into the mould cavity, makes it possible to obtain single crystal unidirectional solidification of the cast article. Such an article would e.g. be particularly useful for creep resistant components, such as a turbine blade.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. Method of manufacturing a ceramic article, the method comprising:
   providing a metal or metal matrix composite preform,
   placing the preform in a heating chamber,
   heating the heating chamber by applying a predetermined time-temperature profile in order to controllably react the preform with a gas introduced into the heating chamber,
   wherein the metal, the gas and the time-temperature profile are chosen so as to induce a metal-gas reaction resulting in at least a part of the preform transforming into a ceramic,
   wherein the time-temperature profile comprises a first oxidation stage in which the heating chamber is heated to below the melting point of the metal to allow metal-gas reaction in order to form a supporting oxide layer at the surface of the metal followed by a second stage in which the heating chamber is heated to a temperature above the melting point of the metal to increase the kinetics of the chemical reaction, wherein the first stage has a duration resulting in a thick enough oxide layer forming so that the article does not slump when heated to more elevated temperatures in the second stage, and a contiguous oxide layer forming so that the not yet reacted metal does not leak out when melting during the second stage,
   wherein there is a third stage in which the heating chamber is heated to a higher temperature than in the second stage so that phase transformation of the ceramic material takes place, and
   wherein the preform is provided by 3D-printing or by 3D-weaving.

2. Method according to claim 1, wherein the preform is 3D-printed using an additive manufacturing method selected from the group consisting of powder-bed, blown-powder and wire-fed.

3. Method according to claim 1, wherein the 3D-printing process deploys one or more heat sources selected from the group consisting of: laser, electron beam, plasma and incoherent light, to melt the metal.

4. Method according to claim 1, wherein the metal pre-form is 3D-printed into a shape selected from the group consisting of: a lattice, an open cellular foam, a porous article, a mould and die.

5. Method according to claim 1, comprising a first stage of oxidation treatment by a chemical, electro-chemical or plasma electrolytic anodising process in order to form a supporting oxide layer at the surface of the metal before the preform is placed in the heating chamber and then placing the preform in the heating chamber, followed by a second stage in which the heating chamber is heated to a temperature above the melting point of the metal to increase the kinetics of the chemical reaction.

6. Method according to claim 1, wherein the metal-gas reaction(s) take place at a gas pressure in the heating chamber of 0.1-10 atm.

7. Method according to claim 1, wherein the preform is fully transformed to make a fully ceramic article.

8. Method according to claim 1, wherein the preform is only partially transformed into ceramic to make a ceramic-metal composite.

9. Method according to claim 8, wherein the partially transformed ceramic-metal composite is further leached in a leaching solution to remove any remaining metal so as to create hollow ceramic tubes.

10. Method according to claim 1, wherein the preform is made of or comprises a material selected from the group consisting of aluminium, zirconium, yttrium, cerium, titanium, hafnium, tungsten, vanadium, niobium, tantalum, beryllium, iron, cobalt nickel, copper, lanthanum, lead, zinc, tin, indium, silicon, germanium, magnesium, calcium and an alloy thereof.

11. Method according to claim 1, wherein the gas introduced into the heating chamber is selected from the group consisting of: is air, oxygen, nitrogen, silane, borane, methane, ammonia, hydrogen, hydrogen sulphide, halogen, phosphine, carbon dioxide and a mixture thereof.

12. Method according to claim 1, wherein the ceramic article is made of a material selected from the group consisting of a metal-oxide, a metal-nitride, a metal-silicide, a metal-boride, a metal-carbide, a metal-hydride, a metal-sulphide, metal-phosphide, metal-halide and a mixed ceramic material.

13. Method according to claim 1, wherein the type of gas in the heating chamber is changed during the process so as to create a layered ceramic article of varying composition.

14. Method according to claim 1, further comprising a subsequent step of reacting the formed ceramic article with acid.

15. Method according to claim 1 further comprising chemically washing an active metal catalyst onto the ceramic article to form a catalytic substrate lattice.

16. Method according to claim 1 further comprising providing the metal or metal matrix preform configured such that the manufactured ceramic article is configured to be used as a medical device, selected from the group consisting of a biomedical implant, an orthopaedic device, an artificial bone structure and a stem-cell scaffold.

17. Method according to claim 1 further comprising providing the metal or metal matrix preform configured such that the manufactured ceramic article is configured to be used for an application selected from the group consisting of RF antenna, dielectric, microwave, embedded sensors and photonic applications.

\* \* \* \* \*